United States Patent [19]

Schubert

[11] Patent Number: 5,345,029

[45] Date of Patent: Sep. 6, 1994

[54] DETERMINING FRACTIONS OF PETROLEUM FUELS BY SUPERCRITICAL FLUID CHROMATOGRAPHY

[75] Inventor: Adam J. Schubert, Placentia, Calif.

[73] Assignee: Atlantic Richfield Company, Los Angeles, Calif.

[21] Appl. No.: 949,198

[22] Filed: Sep. 22, 1992

[51] Int. Cl.$^5$ .......................... C07C 7/12; C10G 25/00
[52] U.S. Cl. .................................. 585/825; 585/826; 208/310 R
[58] Field of Search ............................. 585/825, 826; 208/310 R

[56] References Cited

U.S. PATENT DOCUMENTS 4,124,528  11/1978  Modell ............................ 252/411 R
4,375,387  3/1983   de Filippi et al. .................... 208/321

OTHER PUBLICATIONS

"Standard Test Method for Characteristic Groups in Rubber Extender and Processing Oils and Other Petroleum Derived Oils by the Clay-Gel Absorption Chromatographic Method", American Society for Testing and Materials, Designation: D 2007—91, 1991. (page unavailable).

"Standard Test Method for Separation of Representative Aromatics and Nonaromatics Fractions of High--Boiling Oils by Elution Chromatography", American Society for Testing and Materials, Designation: D 2549—91, 1991. (page unavailable).

"Standard Test Method for Determination of Aromatic Content of Diesel Fuels by Supercritical Fluid Chromatography", American Society for Testing and Materials, Designation: D 5186—91,1991. (page unavailable).

Primary Examiner—Anthony McFarlane
Assistant Examiner—Nhat D. Phan
Attorney, Agent, or Firm—Michael E. Martin

[57] ABSTRACT

Hydrocarbon oils such as diesel fuels, turbine fuels and intermediate distillates may be subjected to quantitative analysis of their saturate, aromatic and polar components by supercritical fluid chromatography using carbon dioxide as the solvent. A sample of the oil is passed into a packed column of silica or the like whereby the respective fractions are separated and retained on the column. Supercritical carbon dioxide at selected pressure and temperature conditions is passed through the column to extract, separately, each of the fractions retained on the column. The extracted fraction and solvent are passed through a restrictor and expanded down to a pressure which will allow the solvent to evaporate and to permit retention or collection of the extracted fraction in a collector arrangement including a selector valve and plural collection containers. Supercritical carbon dioxide is supplied to the column through an injector valve by way of a pump which may be operated to provide the solvent fluid at a selected pressure in accordance with the fraction to be extracted.

8 Claims, 1 Drawing Sheet

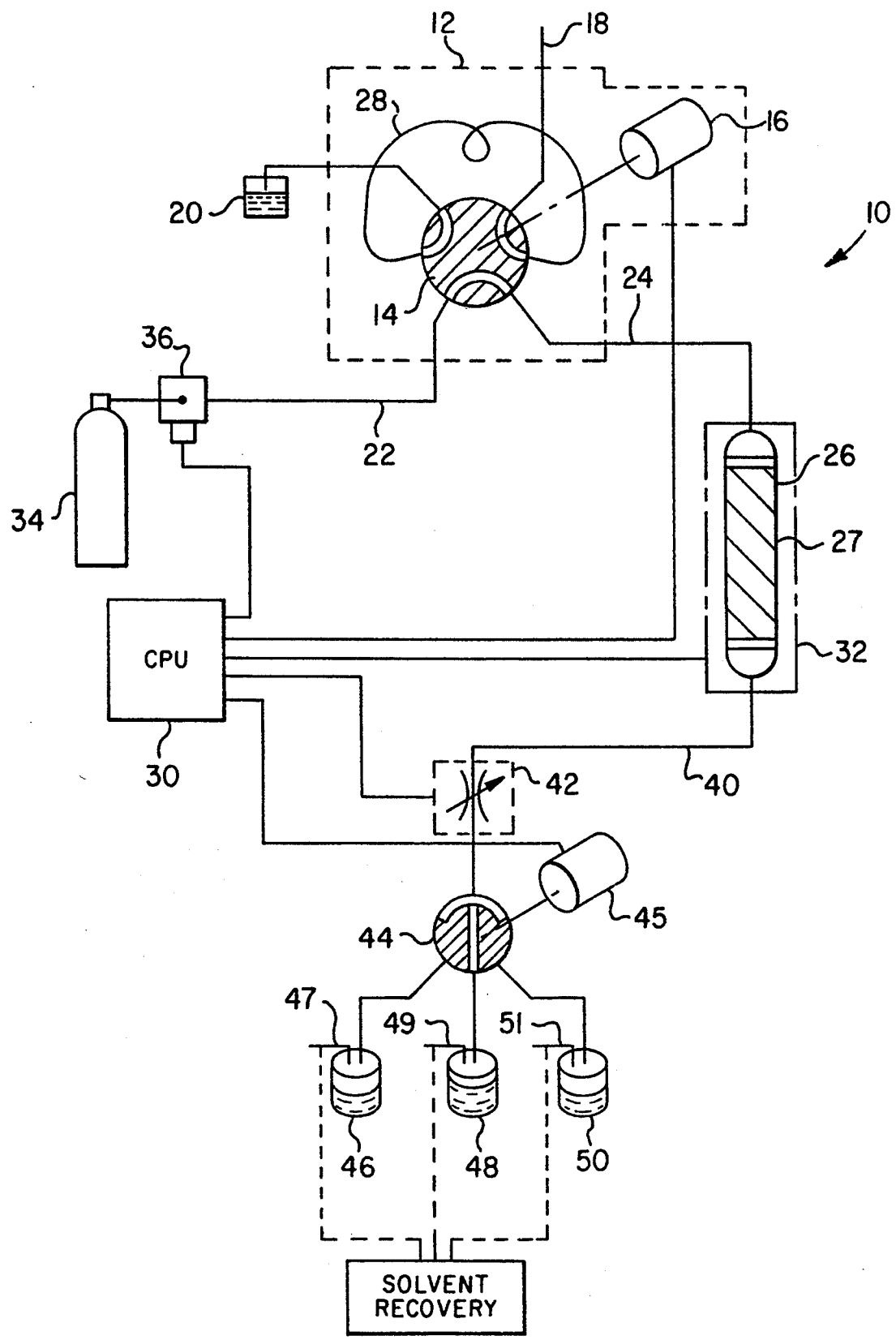

DETERMINING FRACTIONS OF PETROLEUM FUELS BY SUPERCRITICAL FLUID CHROMATOGRAPHY

BACKGROUND OF THE INVENTION

1. Field of the Invention

The present invention pertains to a method of quantitative isolation of representative saturate, aromatic and polar fractions from hydrocarbon oils by preparative scale supercritical fluid chromatography.

2. Background

Several methods exist for analysis of hydrocarbon oils, that is petroleum products which are generally characterized as gas oils, diesel fuels and turbine fuels. Mass spectrometry is widely used, for example, to determine the major fractions generally referred to as saturates, aromatics and polars. These fraction or component names are descriptive of the chemical structure of the hydrocarbons which comprise each of the fractions. The precision and accuracy of the fractionation step is critical to the precision, accuracy and utility of mass spectrometric analysis. Conventional practice requires the separation of the hydrocarbon "oil" or petroleum fuel into the three major components using a technique known as low-pressure liquid chromatography. ASTM Standard Test Method D2007 and ASTM Standard Test Method D2549 are examples of conventional techniques.

Both of the above-mentioned methods use glass columns packed with polar adsorbents such as silica gel, bauxite and clay which are packed by hand for each sample to be analyzed. Column packing is a variable which can have a major impact on the quality of the results of this procedure. Moreover, operator exposure to dust from the packing material is a potential health hazard. The petroleum liquid fractions are separated by successive elution of the column with different organic solvents. This separation technique is time-consuming, labor-intensive, requires significant judgment by the analyst and exposes the analyst to hazardous materials.

A technique known as analytical scale supercritical fluid chromatography is now proposed for use in the petroleum industry according to ASTM Standard Test Method D5186, for example. This technique relies on the use of an on-line detector, such as a flame ionization type detector, which destroys the samples of the separated fractions. Moreover, the sample sizes for analytical scale supercritical fluid chromatography are exceedingly small.

However, the present invention provides a method for determining the major fractions of hydrocarbon oils such as gas oils, diesel fuels, turbine fuels and similar petroleum fuels using a technique which overcomes several disadvantages of the prior art methods including those mentioned hereinabove.

SUMMARY OF THE INVENTION

The present invention provides an improved method for separating and retaining the major fractions of hydrocarbon oils or petroleum fuels utilizing supercritical fluid chromatography.

In accordance with one important aspect of the present invention, hydrocarbon liquids, such as gas oils, diesel fuels and turbine fuels, may be separated into their saturate, aromatic and polar fractions by a packed column type separator and then separately recovered from the column and retained for further analysis. In a preferred embodiment of the invention, the separated fractions of the fuel are retained on the column until separately removed by a single, generally nontoxic solvent, preferably carbon dioxide, which is passed through the column in a supercritical condition which will, respectively, separately remove or elute the major hydrocarbon fractions from the column and carry these fractions to a restrictor and collector apparatus whereby the separated fractions may be reclaimed separately for further laboratory analysis.

In accordance with another important aspect of the present invention, a unique system is provided for use in separating the major fractions of petroleum fuels and the like and separately recovering these fractions for various purposes. The system includes a unique arrangement of a sample injection valve, a separating column, a flow restrictor downstream of the separating column and a collector arrangement for collecting separately the petroleum liquid fractions which have been separated on the column and then eluted from the column by a supercritical fluid solvent.

The method and system of the invention avoids several problems inherent in prior art low-pressure liquid chromatography methodology. For example, the packed column is reusable for a relatively large number of samples, thereby eliminating errors introduced by variations in column characteristics resulting from repeated packing and inconsistencies in packing density. Only one solvent is required for recovery of the separate fractions of the petroleum fluid. In particular, carbon dioxide which is compressed and heated to its supercritical state is a suitable solvent and holds the advantages of being relatively non-toxic, widely available and inexpensive.

Moreover, changes in solvent strength required to perform the fraction recovery method for each separated hydrocarbon fraction is achieved simply by changing solvent density, such as by increasing or decreasing the pressure of the solvent, in its supercritical state. The solvent is easily removed from the separated fractions by merely decompressing the recovered fraction and allowing the solvent to be vented to atmosphere. Since the solvent removal step requires no heating of the sample, but instead actually results in a cooling of the separated sample, the loss of low boiling point components of the various petroleum fluid fractions is minimized. Still further, the method and system of the present invention provides for automation of the separation and recovery process which would allow groups of samples to be separated under computer control and on a substantially continuous basis.

The above-noted features and advantages of the present invention, together with other superior aspects thereof, will be further appreciated by those skilled in the art upon reading the detailed description which follows in conjunction with the drawing.

BRIEF DESCRIPTION OF THE DRAWING

The drawing is a schematic diagram of a hydrocarbon oil (petroleum fuel) supercritical fluid chromatography system in accordance with the present invention.

DESCRIPTION OF PREFERRED EMBODIMENTS

In the production and use of certain hydrocarbon oils, also referred to herein as petroleum fuels or hydrocarbon liquids, the composition of the fuel as regards the quantity of so-called saturate, aromatic and polar components is important with respect to the use of the fuel and its emission characteristics. Accordingly, analysis of such fuels is also important so that adjustments to refining processes may be made, if necessary, the addition of certain additives may be considered, and handling and transport conditions may be adjusted and controlled. Although standard test methods have been proposed as mentioned hereinabove for determining the aromatic content of diesel fuels, for example, the proposed methods do not address the separation of such fuels into all of the major fractions and the proposed procedures do not satisfy the requirement for recovery and retention of the separated fractions. The system illustrated in the drawing figure and the method described herein provide these desired improvements.

A preferred arrangement of a system in accordance with the present invention is illustrated in the drawing figure. Various substitutions and modifications may be made in accordance with the invention. A preferred embodiment of the system, is generally designated by the numeral 10 and includes, as a major component, a sample injector valve, generally designated by the numeral 12. The sample injection valve may be of a type manufactured by Valco as their Model C6UW. Typically, the injector valve 12 includes a motor-operated closure member 14 which is controlled by a suitable motor 16 to be rotated to one of three positions illustrated and described herein. The injector valve 12 is adapted to be in communication with a source, not shown, of petroleum fuel to be analyzed by way of a conduit 18. The injector valve 12 is also adapted to be in communication with a waste tank 20. Still further, the injector valve 12 is operable to be in communication with a source of a suitable solvent by way of a conduit 22. A conduit 24 is in communication with the valve closure member 14 for conducting a sample of fluid to be analyzed, as well as solvent, to a packed column, generally designated by the numeral 26. Finally, the injector valve 12 also includes a conduit 28, which may be incorporated therein as part of the injector valve, for holding a predetermined volume of a sample of the petroleum fuel to be analyzed.

Operation of the valve 12 as well as other components of the system 10 to be described in detail herein may be automatically controlled by a central processing unit or computer 30. In the position of the valve closure member 14 illustrated, solvent and/or a transport fluid may be communicated through the valve 12 to the column 26 by way of conduits 22 and 24. In this same position of the valve, as illustrated, a sample of petroleum fuel to be analyzed is conducted by way of the conduit 18, through the closure member 14 and into the sample holding conduit or "loop" 28. The conduit 28 is suitably flushed to be sure that a complete sample is available for injection into the column 26 by placing the conduit 28 in communication with the waste tank 20 by way of the valve 12, as illustrated. When it is desired to inject a sample of petroleum fuel into the column 26, the valve closure member 14 is rotated in a clockwise direction to a position such that the conduit 28 is in communication with the conduit 24 and the conduit 22 is in communication with the conduit 28 so that the liquid sample may be injected into the column by a transport medium which may comprise the solvent to be described herein. In the just-described position, the conduit 18 is also placed in communication with the waste tank 20 whereby any excess amount of hydrocarbon liquid sample which is supplied to the valve 12 may be collected. The conduit 28 is, of course, full of a measured quantity of the liquid to be analyzed prior to movement of the valve 12 from the position shown to the position whereby the conduit 28 is placed in communication with the conduit 24.

The column 26 is preferably a pre-packed type which includes a suitable pressure vessel 27 which is preferably disposed in a temperature controlled enclosure 32. The enclosure 32 is preferably provided with suitable means, not shown, operable to maintain the column 26 at a predetermined temperature, and also suitably controlled by the CPU 30. The column 26 is preferably packed with a suitable packing such as silica or a packing supplied by Suprex Corporation, Pittsburgh, Pennsylvania under the designation PetroPack type packing. Placement of a sample of petroleum fuel or other hydrocarbon liquid to be separated on the column 26 is accomplished by a transport medium and solvent supplied from a source 34 by way of a pump 36 in communication with the conduit 22. The pump 36 may be of a type which is operable to supply solvent fluid to the conduit 22 at a selected output pressure, which pressure may be varied. In this regard, the pump 36 may be of a type also supplied by Suprex Corporation under the designation VariPump. Alternatively, suitable pressure regulation means may be interposed in the conduit 22 between the pump 36 and the injection valve 12.

The transport and solvent medium from source 34 may be carbon dioxide, preferably of supercritical fluid chromatographic grade, such as 99.999+ percent minimum purity, and supplied in a pressurized cylinder, such as the source 34, equipped with a dip tube for removal of liquid carbon dioxide.

The system 10 further includes conduit means 40 connected to the column 26 and having interposed therein suitable restrictor means 42 for controlling the flow of fluid from the column 26 to a collector arrangement for collecting samples of the separated fractions of the petroleum fuel which have deposited on the column packing. The restrictor 42 is illustrated as a variable orifice and may comprise either a variable or fixed orifice or a lengthy, relatively small-diameter tube capable of maintaining mobile phase supercritical conditions within the column 26 and up to the fraction collector means.

The collector means preferably includes a selector valve 44 which may be positioned to provide for collection of samples of the saturate, aromatic and polar fractions of the fuel being analyzed in separate containers 46, 48 and 50. The containers 46, 48 and 50 are preferably closed, but ventable at vent conduits 47, 49 and 51, respectively, to allow the solvent vapors to escape while retaining the petroleum fraction collected therein. Alternatively, the solvent may be separately recovered by means connected to the vent conduits 47, 49 and 51. The selector valve 44 is preferably motor operated by a motor 45 which may also be controlled by the CPU 30.

The components of the system 10 are sized to provide respective sample volumes (about 1 milliliter) to the containers 46, 48 and 50 of the respective fractions of the hydrocarbon liquid being analyzed. Accordingly, the total volume of the column 26 is selected to be proportional to the volume of the sample of hydrocarbon liquid injected by the injector valve 12. The solvent is supplied to the column 26 at conditions above the solvent critical pressure and temperature, for example, at temperatures above 35° C. and pressures exceeding 70 atmospheres. Generally, the operation of the system 10 may be automated by the CPU 30 to provide a sample of petroleum fuel by way of the injector 12 to the column 26, by transport medium, such as the carbon dioxide solvent, and allowing the sample to reside on the column a sufficient period of time to provide for separation of the saturate, aromatic and polar components onto the column packing. Additional carbon dioxide solvent is then supplied in a supercritical state by way of the pump 36 and the injector valve 12 to the column 26 at selected pressures and temperatures which will strip the desired component or "fraction" from the column packing and transport the stripped fraction through the restrictor 42 and into a selected one of containers 46, 48 and 50. The position of the valve 44 will, accordingly, be coordinated with the selected operating pressure and temperature of the solvent being injected into the column 26. The pressure of the solvent is controlled by pump 36.

Preparation of the samples of hydrocarbon oil (petroleum fuel) to be analyzed may include making a volume dilution of a sample with a suitable diluent such as carbon disulfide.

Those skilled in the art will recognize that the system 10 and the method described hereinabove hold several advantages previously discussed. Moreover, the improved method and system eliminates the requirement to use volatile solvents which must be carefully evaporated without loss of the more volatile components of each of the fractions of the hydrocarbon liquid being analyzed to ensure quantitative recovery of these fractions. The separation process is easily automated and does not require operator attention and flow adjustments. Control and disposal of the mobile phase solvent in the form of carbon dioxide, in particular, is easier to accomplish and does not result in the loss of components of the hydrocarbon liquid fractions which are being separated and collected. Time-consuming emptying and cleaning of conventional separation columns is also eliminated.

Although preferred embodiments of a method and system in accordance with the present invention have been discussed herein, those skilled in the art will recognize that further substitutions and modifications may be made without departing from the scope and spirit of the invention as recited in the appended claims.

What is claimed is:

1. A method for separating and recovering at least one fraction of a hydrocarbon oil comprising the steps of:
   providing a sample of said hydrocarbon oil;
   separating said sample in a separation means into at least one fraction consisting of saturates, aromatics, or polars and retaining said separated fraction on said separation means;
   flowing a solvent comprising a fluid in a supercritical state through said separation means to remove said separated fraction from said separation means;
   passing said solvent and said separated fraction through means for reducing the pressure of said solvent; and
   passing said solvent and said separated fraction to a collector means for collecting said separated fraction while separately recovering said solvent in vapor phase resulting from said reduction in pressure.

2. The method set forth in claim 1 wherein: said separation means is a packed column.

3. The method set forth in claim 2 including the step of:
   separating said sample into fractions of saturates, aromatics, and polars and retaining each of said fractions on said separation means.

4. The method set forth in claim 3 including the step of:
   separately removing each of said fractions from said column by passing a quantity of said solvent through said column at a pressure and temperature that cause said solvent to remain in said supercritical state and selectively remove said fractions from said column.

5. The method set forth in claim 4 including the step of:
   passing said solvent together with said separated fractions through a restrictor means for reducing the pressure of said solvent sufficiently to vaporize said solvent and collecting said separated fractions substantially free of said solvent at said restrictor means.

6. A method for separating and recovering plural fractions of a hydrocarbon fuel, said fractions comprising saturate, aromatic, and polar components of said petroleum fuel, said method comprising the steps of:
   passing a sample of said fuel onto a packed column to separate said sample into said fractions on said column;
   passing a quantity of a solvent through said column at a first supercritical condition of said solvent to extract one of said fractions from said column;
   passing said solvent with said extracted fraction through a restrictor means to reduce the pressure of said solvent and said extracted fraction to allow said solvent to vaporize without vaporizing said extracted fraction;
   collecting said extracted fraction in liquid form while permitting said solvent vapor to escape from said extracted fraction;
   providing said solvent at a second supercritical condition and passing said solvent through said column at said second supercritical condition to extract another of said fractions from said column; and
   providing said solvent at a third supercritical condition and passing said solvent through said column at said third supercritical condition to extract still another of said fractions from said column.

7. The method set forth in claim 6 wherein: said solvent is carbon dioxide.

8. A method for separating and recovering at least one fraction of a hydrocarbon oil, comprising the steps of:
   providing a sample of said hydrocarbon oil;
   subjecting said sample to separation means to separate at least one fraction consisting of saturates, aromatics, or polars and retaining said separated fraction on said separation means;
   flowing a solvent comprising a fluid in a supercritical state through said separation means to remove said separated fraction from said separation means;
   passing said solvent and said separated fraction through means for reducing the pressure of said solvent; and
   passing said solvent and separated fraction to collector means for collecting said separated fraction while separately venting said solvent in vapor phase to atmosphere.

* * * * *